(12) United States Patent
He et al.

(10) Patent No.: US 8,309,486 B2
(45) Date of Patent: Nov. 13, 2012

(54) COMPOSITE SOLID ACID CATALYST, PREPARING PROCESS AND APPLICATION IN THE ALKYLATION

(75) Inventors: Yigong He, Beijing (CN); Zheng Man, Beijing (CN); Xuhong Mu, Beijing (CN)

(73) Assignees: China Petroleum Chemical Corporation, Beijing (CN); Research Institute of Petroleum Processing, Sinopec, Beijing (CN)

( * ) Notice: Subject to any disclaimer, the term of this patent is extended or adjusted under 35 U.S.C. 154(b) by 0 days.

(21) Appl. No.: 12/915,534

(22) Filed: Oct. 29, 2010

(65) Prior Publication Data

US 2011/0100876 A1 May 5, 2011

(30) Foreign Application Priority Data

Oct. 29, 2009 (CN) .......................... 2009 1 0209531
Oct. 29, 2009 (CN) .......................... 2009 1 0209532
Oct. 29, 2009 (CN) .......................... 2009 1 0209533

(51) Int. Cl.
*B01J 27/00* (2006.01)
*B01J 27/182* (2006.01)
*B01J 27/188* (2006.01)
*B01J 27/19* (2006.01)

(52) U.S. Cl. ......... 502/211; 502/208; 502/210; 502/214
(58) Field of Classification Search .................. 502/208, 502/210, 211, 214
See application file for complete search history.

(56) References Cited

U.S. PATENT DOCUMENTS

| 2,173,187 | A | * | 9/1939 | Tanner ........................... 568/896 |
| 5,324,881 | A | * | 6/1994 | Kresge et al. .................. 585/721 |
| 6,040,262 | A | * | 3/2000 | Fougret et al. ................. 502/162 |
| 6,534,435 | B1 | * | 3/2003 | Prasad et al. .................. 502/208 |
| 7,674,945 | B2 | * | 3/2010 | He et al. ........................ 585/731 |
| 2007/0118005 | A1 | | 5/2007 | He et al. |

OTHER PUBLICATIONS

"The effect of trace amounts of promoter on the selectivity of catalyst in the solid acid alkylation," Yigong He et al. Applied Catalysis A 268 (2004), pp. 115-119.*
"Synthesis, characterization and catalytic activity of new solid acid catalysts, H3PW12O40 supported on to hydrous zirconia," Shirish Patel et al. Journal of Molecular Catalysis A: Chemical 192 (2003), pp. 195-202.*

* cited by examiner

*Primary Examiner* — Patricia L Hailey
(74) *Attorney, Agent, or Firm* — Scully, Scott, Murphy & Presser, P.C.

(57) ABSTRACT

The present invention provides a composite solid acid catalyst consisting of from 50%-80% by weight of a porous inorganic support, from 15% to 48% by weight of a heteropoly compound loaded thereon, and from 2% to 6% by weight of an inorganic acid. The present invention further provides a process for preparing said composite solid acid catalyst and a process for conducting an alkylation reaction by using such catalyst. The composite solid acid catalyst of the present invention has the acid sites type of Brönsted acid and has an acid sites density of not less than $1.4 \times 10^{-3}$ mol $H^+/g$. Moreover, said composite solid acid catalyst has the homogeneous acid strength distribution, and is a solid acid catalyst having excellent performances.

20 Claims, No Drawings

COMPOSITE SOLID ACID CATALYST, PREPARING PROCESS AND APPLICATION IN THE ALKYLATION

FIELD OF THE INVENTION

The present invention relates to a composite solid acid catalyst, process for preparing the same and use thereof in the alkylation reaction. Specifically, the present invention relates to a composite solid acid catalyst simultaneously containing an inorganic acid and a heteropoly compound, process for preparing the same and use thereof in the alkylation reaction.

BACKGROUND OF THE INVENTION

In the petrochemical catalysis field, acidic catalytic materials are used as the catalyst in most hydrocarbon conversion reactions, such as cracking reaction, alkylation, reforming reaction, stacking reaction, isomerization, disproportionation reaction and the like (HOU Xianglin, *Oil Refining Technologies in China*, China Petrochemical Press, 1991). Thus acidic catalytic materials play a very important role in the petrochemical catalysis field. Research and development of acidic catalytic materials having higher performances are the important tasks for scientific research works.

The acidity properties of the acidic catalytic materials primarily include acid sites density, acid strength, acid sites type (Brönsted acid or Lewis acid), and have a notable and important effect on the catalytic reaction in which the acidic catalytic materials are used as the catalyst (WU Yue, *Catalysis Chemistry*, Science Press, Beijing, 2000, pages 162-196; HAN Weiping, *Introduction of Catalysis Chemistry*, Science Press, Beijng, 2003, pages 172-238; HUANG Zhongtao, ZENG Zhaohuai, *Catalysis During Petrochemical Process*, China Petrochemical Press, Beijing, 1995, pages 209-253). The acid sites density of the acidic catalyst plays an essential role in the hydrocarbon conversion reactions, such as cracking reaction, alkylation reaction and the like, and it can greatly improve the reaction selectivity (HE Mingyuan, *Green Chemistry Related to Petroleum Refining and Petrochemical Production*, China Petrochemical Press, Beijing, 2005, pages 109-169). The acidic catalytic materials can be classified into two types, i.e. liquid acids such as sulfuric acid, hydrofluoric acid and the like, and solid acids such as molecular sieve, superacid, loading-type acid catalytic material, acidic ion resin and the like. Liquid acids have a very high acid sites density (calculated by mol H$^+$/g), and all are Brönsted acid sites. Generally, the acid sites density of the solid acids is less than the acid sites density of the liquid acids by two orders of magnitude because of structural restriction. The acid sites density of almost all solid acid catalytic materials prepared according to the prior art cannot reach to the order of magnitude of the liquid acid. The acidity properties of the liquid acid and solid acid catalysts are listed in Table 1.

TABLE 1

Acidity properties of the acid catalyst

| Acid-catalytic materials | Acid sites density (mol H$^+$/g) | Acid strength (−H$_o$) | Acid sites type |
|---|---|---|---|
| Sulfuric acid (100%) | 20 × 10$^{-3}$ | 11.99 | B |
| HF (100%) | 50 × 10$^{-3}$ | — | B |
| USY molecular sieve catalyst (Si/Al = 3) | 0.4 × 10$^{-3}$ | — | B and L |

TABLE 1-continued

Acidity properties of the acid catalyst

| Acid-catalytic materials | Acid sites density (mol H$^+$/g) | Acid strength (−H$_o$) | Acid sites type |
|---|---|---|---|
| Superacid SO$_4$$^{-2}$/ZrO$_2$ | 0.1 × 10$^{-3}$ | 14.52 | B and L |
| H$_3$PW$_{12}$O$_{40}$/SiO$_2$ (having a loading capacity of 25%) | 0.26 × 10$^{-3}$ | 13.16 | B |
| highly acidic ion resin | 0.45 × 10$^{-3}$ | 10.10 | B and L |

B: Brönsted acid;
L: Lewis acid

CONTENTS OF THE INVENTION

The object of the present invention is to provide a composite solid acid catalyst, process for preparing the same and use thereof in the alkylation reaction. Specifically, the present invention relates to a composite solid acid catalytic material obtained by enabling an inorganic acid to be loaded on the porous inorganic support on which a heteropoly compound is loaded and simultaneously containing an inorganic acid and a heteropoly compound, wherein the catalytic material has the acid sites which all are Brönsted acid and has a higher acid sites density.

Heteropoly compounds are the inorganic compounds having the cage-type structure and tunnel and obtained by acidification, condensation and dehydration of two or more inorganic oxygen-containing acid radical ions, and such inorganic compounds have a strong acidity. Heteropoly compounds include heteropoly acids and heteropoly acid salts. Heteropoly acids are the compounds obtained by totally or partially replacing H$^+$ of the heteropoly acids with alkali metal ions, alkali earth metal ions or ammonium ions. Due to its small specific surface area, heteropoly compounds are not suitable for separate application as the solid acid catalyst, and heteropoly compounds are commonly loaded onto the porous support having a high specific surface area (see CN1232814A and U.S. Pat. No. 5,324,881). Heteropoly compounds consist of cations and anions, wherein anions have a very large molecular size (1.23 nm), so that a greater accumulation space is formed between the anions of the heteropoly compounds.

Upon research, it is found that, when the inert hydrocarbons, such as saturated alkanes and cycloalkanes, in which a certain amount of the inorganic acids are dissolved, contact with the porous inorganic support material on which the heteropoly compounds are loaded, these inorganic acids dissolved in the inert hydrocarbons and having a small molecular size (the molecular size of HF being 0.13 nm, and the molecular size of HCl being 0.18 nm) can be absorbed into the accumulation space formed by the heteropoly compound anions having a macromolecular size (1.23 nm) In the accumulation space, H$^+$ in these inorganic acid molecules and H$^+$ of the heteropoly acids per se together build up the acid sites of the solid acid catalytic material. Moreover, these acid sites all are the typical Brönsted acid sites. As compared with the solid acid catalytic material prepared according to the prior art, such composite solid acid catalytic material has a higher acid sites density of not less than 1.4×10$^{-3}$ mol H$^+$/g, and said acid sites have the homogeneous acid strength distribution.

The present invention provides a composite solid acid catalyst consisting of from 50% to 80% by weight of a porous inorganic support, from 15% to 48% by weight of a heteropoly compound loaded thereon, and from 2% to 6% by weight of an inorganic acid, said heteropoly compound generally being an inorganic compound represented by the general formula of $M_xH_{8-n-x}[AB_{12}O_{40}]$, wherein A represents P or Si atom, referred to as the central atom or heteroatom, B represents Mo or W atom, referred to as the polyatom, M represents selected from the group consisting of alkali metals of Li, Na, K, Rb and Cs, alkali earth metals of Be, Mg, Ca, Sr and Ba, and $NH_4$, n is the valence state of A, which is 4 or 5, and x is any number from 0 to 4.

In the composite solid acid catalyst according to the prevent invention, said porous inorganic support is selected from the group consisting of silicon oxide, alumina, active carbon, magnesium oxide, titanium oxide, natural or artificially synthetic aluminosilicate zeolite, molecular sieve, carbon fiber and natural clay, or mixtures thereof. Said zeolite and molecular sieve may be selected from the group consisting of A-type zeolites, X-type zeolites, Y-type zeolites, mordenite, ZMS-series zeolites, Beta zeolites, offretite zeolites, Ω zeolites, aluminophosphate molecular sieve, titanium silicalite molecular sieve, or mixtures thereof. Said clay may be the unstratified clays such as kaolin, diatomite, or the expandable stratified clays such as montmorillonite, diatomite, rectorite and the like. The porous inorganic support is preferably one or more selected from the group consisting of active carbon, silicon oxide, alumina and zeolite, more preferably silicon oxide. The porous inorganic support is in an amount of from 50% to 80% by weight of the composite solid acid catalyst.

The present invention provides a composite solid acid catalyst, wherein, in the general formula of the heteropoly compound, A is P; B is W; M is selected from the group consisting of alkali metal ions such as Li, Na, K, Rb, Cs ion, alkali earth metal ions such as Be, Mg, Ca, Sr, Ba ion or $NH_4$.

In a more preferred solution, A is P; B is W; M is selected from the group consisting of Cs, K and $NH_4$.

In the general formula of the heteropoly compound, x is any number from 0 to 4, preferably from 2 to 4. Said heteropoly compound is a heteropoly acid when x is 0, or a heteropoly acid salt when x is greater than O, Said heteropoly acid is generally selected from the group consisting of phosphotungstic acid, phosphomolybdic acid, silicotungstic acid and silicomolybdic acid, preferably phosphotungstic acid. The heteropoly acid salt is preferably an alkali metal salt or alkali earth metal salt, preferably an alkali metal salt, more preferably K or Cs salts, of a heteropoly acid, wherein one preferred heteropoly acid salt is a K or Cs salt of phosphotungstic acid.

The present invention provides a composite solid acid catalyst, wherein the heteropoly compound is in an amount of from 15% to 48%, preferably from 20% to 40 wt % by weight of the composite solid acid catalyst.

The present invention provides a composite solid acid catalyst, wherein the inorganic acid is HF or HCl in an amount of from 2% to 6%, preferably from 2% to 5% by weight of the composite solid acid catalyst.

The present invention provides a composite solid acid catalyst, wherein the acid sites type is Brönsted acid and the acid sites density is not less than $1.4 \times 10^{-3}$ mol $H^+$/g.

The present invention further provides a process for preparing a composite solid acid catalyst, comprising the steps of (1) loading a heteropoly compound onto a porous inorganic support to obtain a heteropoly compound-loaded material, wherein said heteropoly compound having a general formula of $M_xH_{8-n-x}[AB_{12}O_{40}]$, in which A is a heteroatom P or Si, B is polyatom W or Mo, M is selected from the group consisting of alkali metals of Li, Na, K, Rb and Cs, alkali earth metals of Be, Mg, Ca, Sr and Ba, and $NH_4$, n is the valence state of A, which is 4 or 5, x is any number from 0 to 4, and said porous inorganic support is one or more selected from silicon oxide, alumina, active carbon, magnesium oxide, titanium oxide, natural or artificially synthetic aluminosilicate zeolite, molecular sieve, carbon fiber and natural clay, or mixtures thereof; and said porous inorganic support is in an amount of from 50% to 80% by weight, and the amount of the loaded heteropoly compound ranges from 15% to 48% by weight, relative to the weight of the composite solid acid catalyst;

(2) dissolving an inorganic acid selected from HF or HCl in hydrocarbons including saturated alkanes, cycloalkanes, aromatic hydrocarbons or petroleum ethers; and (3) contacting said hydrocarbons comprising the inorganic acid with the heteropoly compound-loaded material to obtain a composite solid acid catalyst simultaneously comprising the inorganic acid and the heteropoly compound, wherein the amount of the loaded inorganic acid ranges from 2% to 6% by weight relative to the weight of the composite solid acid catalyst.

The amount of the loaded inorganic acid may be controlled by the concentration of the inorganic acid in the inert hydrocarbons, the contacting temperature, the contacting pressure, the flow rate of the inert hydrocarbons, and the contacting time.

The heteropoly compound in the preparation process according to the present invention is a heteropoly acid or a heteropoly acid salt, wherein said heteropoly acid is generally selected from the group consisting of phosphotungstic acid, phosphomolybdic acid, silicotungstic acid and silicomolybdic acid, preferably phosphotungstic acid; said heteropoly acid salt is preferably an alkali metal salt or alkali earth metal salt, preferably an alkali metal salt, more preferably K or Cs salts, of a heteropoly acid, and one preferred heteropoly acid salt is a K or Cs salt of phosphotungstic acid.

The porous inorganic support in the preparation process according to the present invention is selected from the group consisting of silicon oxide, alumina, active carbon, magnesium oxide, titanium oxide, natural or artificially synthetic aluminosilicate zeolite, molecular sieve, carbon fiber and natural clay, or mixtures thereof. Said zeolite and molecular sieve may be selected from the group consisting of A-type zeolites, X-type zeolites, Y-type zeolites, mordenite, ZMS-series zeolites, Beta zeolites, offretite zeolites, Ω zeolites, aluminophosphate molecular sieve, titanium silicalite molecular sieve, or mixtures thereof. Said clay may be the unstratified clays such as kaolin, diatomite, or the expandable stratified clays such as montmorillonite, diatomite, rectorite and the like. The porous inorganic support is preferably one or more selected from the group consisting of active carbon, silicon oxide, alumina and zeolite.

The hydrocarbons in the preparation process according to the present invention are inert, i.e. they are used merely as the carrying agent and do not chemically react with any heteropoly compound or support during the preparation. Said hydrocarbons include saturated alkanes, cycloalkanes, aromatic hydrocarbons and petroleum ethers, preferably propanes, n-butanes, isobutanes, pentanes, hexanes, cyclopentanes, cyclohexanes, benzene, toluene and xylene.

The inorganic acid in the preparation process according to the present invention is HF or HCl, or mixtures thereof.

The process for preparing a composite solid acid catalytic material provided in the present invention may be carried out in a general device. After the preparation, the composite solid acid catalytic material is discharged and stored under the protection of inert gases. The preparation process provided in the present invention can also be carried out in the same reactor in which the composite solid acid catalytic material is used for the catalytic reaction, wherein the composite solid acid catalytic material after the preparation can be used for the subsequent catalytic reaction without being discharged.

In the process for preparing a composite solid acid catalytic material provided in the present invention, loading the heteropoly compound onto the porous inorganic support in step (1) is the conventional immersion method for preparing a supporting-type catalytic material. The specific steps include:
  (A) treating a certain amount of the porous inorganic support powder or the shaped porous inorganic support particles for 0.5-2.0 h at 20-100° C., and cooling to room temperature;
  (B) impregnating the porous inorganic support in a certain amount of the heteropoly acid solution at normal pressure for 0.2 to 4.0 h;
  (C) drying at normal atmosphere and under the inert atmosphere for 10 to 35 h at 30-200° C., preferably 50-150° C., wherein said inert atmosphere represents the atmosphere, such as nitrogen gas, which does not react with the heteropoly acid or support, such as nitrogen gas, to obtain a support-heteropoly acid material; the amount of the loaded heteropoly acid generally ranges from 15% to 48 wt %, preferably from 20% to 40 wt %.

Said loaded heteropoly acid material may directly and subsequently contact with the hydrocarbons containing inorganic acids, or the conventional immersion method can be used to contact said loaded heteropoly compound material with the solution of alkali metal salts, alkali earth metal salts or ammonium salts, so as to convert a part of the loaded heteropoly acids into the heteropoly acid salts. The specific steps include formulating the corresponding salt solution according to the stoichimetrical formula of the heteropoly acid salts to be obtained, impregnating the heteropoly acids-loaded material with such salt solution for 0.2 to 3.0 h, reacting the heteropoly acids on the porous inorganic support with the corresponding salt solution to produce the corresponding heteropoly acid salts, so as to obtain a heteropoly acid salt-loaded material. The amount of the loaded heteropoly acid salt ranges from 15% to 48 wt %, preferably from 20% to 40 wt %. Then the resultant heteropoly acid salt-loaded material is in contact with the hydrocarbons containing the inorganic acids. Said alkali metal salts or ammonium salts are preferably carbonates of K, Cs or $NH_4$.

In the process for preparing a composite solid acid catalytic material provided in the present invention, carrying the inorganic acid with the inert hydrocarbons involves dissolving the inorganic acid in the inert hydrocarbons, wherein the content of the inorganic acid in the inert hydrocarbons at most can reach the saturation concentration of the inorganic acid in the inert hydrocarbons, preferably from 20 to 2,000 ppm calculated by $H^+$, more preferably 100 to 1,500 ppm, calculated by H. After being in contact with the inorganic support material on which the heteropoly compound is loaded, the amount of the loaded inorganic acid generally ranges from 1% to 6 wt %, preferably from 2% to 5 wt %, along with the changes of the contacting conditions.

In the process for preparing a composite solid acid catalytic material provided in the present invention, carrying the inorganic acid with the inert hydrocarbons and contacting with the inorganic support material on which the heteropoly compound is loaded can be conducted in a fixed-bed reactor, a batch tank reactor, a moving bed or a triphase slurry bed reactor. When the inorganic support material on which the heteropoly compound is loaded is the shaped particles, a fixed-bed rector is preferred, and a metering pump is used to flow the inert hydrocarbons in which the inorganic acid is dissolved through said shaped particle bed layer. Said contacting temperature ranges from 20 to 250° C., preferably from 30 to 200° C.; the pressure ranges from 0.05 to 7.0 MPa, preferably from 0.1 to 6.0 MPa; the weight space velocity of the inert hydrocarbons carrying the inorganic acid ranges from 0.1 to 10.0 $h^{-1}$, preferably from 1.0 to 8.0 $h^{-1}$; the contacting time ranges from 1 to 120 h, preferably from 4 to 80 h.

When the inorganic support material on which the heteropoly compound is loaded is the fine particle powder, a batch tank reactor, is preferably used to mix, stir and contact the inert hydrocarbons in which the inorganic acid is dissolved with said fine particle powder.

In order to prevent water from affecting the composite solid acid catalytic material, the inorganic support material on which the heteropoly compound is loaded can be treated with the inert gases before the inorganic acid is loaded, i.e. passing the inert gases (such as nitrogen gas) through inorganic support material on which the heteropoly compound is loaded for 1 to 50 h at normal pressure and at 50-200° C., preferably 80-160° C.

According to the preparation process provided in the present invention, the solid acid catalytic material having a high acid sites density can be obtained, wherein the amount of the loaded inorganic acid ranges from 2% to 6 wt %; the amount of the loaded heteropoly compound ranges from 15% to 48%, and the remaining being the inorganic support material. The acid sites thereof all are Brönsted acid, and the acid sites density thereof is not less than $1.4 \times 10^{-3}$ mol $H^+$/g, which is higher than the solid acid material prepared according to the prior art by an order of magnitude. Moreover, said acid sites have the homogeneous acid strength distribution. The preparation process according to the present invention protects the preparation procedures from external environments, and the resultant composite solid acid catalytic material can be directly used for the catalytic reaction, so as to avoid the procedures such as transition, storage, transportation and the like and to maintain a high catalytic activity and selectivity.

The present invention further provides a process for conducting an alkylation reaction by using such composite solid acid catalyst, wherein the composite solid acid catalyst obtained by the preparation process according to the present invention can be used in the same reactor for the subsequent catalytic reaction without being discharged. Alternatively, the composite solid acid catalyst is discharged under the protection of the inert gases after the preparation and stored for standby application, so as to conduct the catalytic alkylation reaction in other reactors. Generally, the reaction temperature ranges from 35-180° C.; the reaction pressure ranges from 0.8 to 8.0 MPa; the weight space velocity ranges from 0.5 to 15 $h^{-1}$; and the alkane/olefin molar ratio ranges from 10 to 350.

MODES OF CARRYING OUT THE INVENTION

The present invention has been completely disclosed above. The following examples further state the process provided in the present invention, but the present invention will not be limited in this way.

phosphotungstic acid, phosphomolybdic acid, silicotungstic acid and silicomolybdic acid are analytically pure (produced by Tianjin Fine Chemical Co., Ltd); silicon oxide is produced by Qingdao Haiyang Chemical Co., Ltd; cesium carbonate and potassium carbonate are analytically pure (produced by Beijing Chemical Plant); active carbon is produced by Beijing Guanghua Timber Mill; and γ-alumina is produced by Hunan Changling Catalyst plant.

X-fluorescence quantitative analysis method is used to determine the mass content % of F (abbreviated as $F_{w\%}$) and Cl (abbreviated as $Cl_{w\%}$) respectively in the sample of composite solid acid. The capacity of the heteropoly acid is abbreviated as S %. The molecular weight of the heteropoly acid is M. The molecular weight of F is 19. The acid sites density (mol $H^+$/g) of the composite solid acid material is calculated according to those data.

The $H^+$ mol in the heteropoly acid supported on the composite solid acid catalytic material per grain is 3×(S %/M). The F mol absorbed by the heteropoly acid supported on the composite solid acid catalytic material per gram is F %/19. The total $H^+$ mol in the composite solid acid catalytic material per gram is 3×(S %/M)+F %/19.

The acid strength Ho of the composite solid acid catalytic material is determined by the following method. 0.7 g of the sample was placed in a small glass weighing bottle, and then placed in a three-necked glass bottle. The temperature of the sample could be controlled by heating the three-necked glass bottle with a heating jacket which could accurately control the temperature. Meanwhile, the sample was vacuumized so as to completely remove water therein. The indicator was placed in the indicator dropping bottle at the center of the three-necked bottle. Then the glass cock thereon was slowly turned on to drop the indicator onto the sample so as to observe the color change. The acid strength Ho of the sample was determined according to the color change of the sample. The indicator was the corresponding solution containing 0.5% by weight of the indicator and formulated with the dried cyclohexane as the solvent.

Examples 1-11 specifically states the preparation process of the present invention.

Example 1

14.0 g of $H_3PW_{12}O_{40} \cdot 22H_2O$ was weighed and dissolved in 88.0 ml of deionized water to formulate a phosphotungstic acid solution. 37 g of silica gel $SiO_2$ having a particle size of 20-40 meshes was fed into the phosphotungstic acid solution. After dipping for 1.0 h, then drying in a drying oven for 12 h at 80° C., a heteropoly acid-loaded material containing 25% by weight of $H_3PW_{12}O_{40}$ and 75% by weight of silica gel was obtained and labeled as 25% HPW/$SiO_2$.

10.0 g of 25% HPW/$SiO_2$ was loaded into a fixed bed reactor. At normal pressure and at 110° C., nitrogen gas flowed through 25% HPW/$SiO_2$ bed layer for 5 h. After the treatment, the temperature was decreased to 95° C. Under the conditions of a temperature of 95° C., a pressure of 2.5 MPa, and a weight space velocity of 1.0 $h^{-1}$ at which isobutanes flowed through 25% HPW/$SiO_2$ bed layer, isobutanes containing 1450 ppm HF were pumped via a metering pump into the fixed bed reactor for 8 h. Upon purging with highly pure nitrogen gas, the composite solid acid catalytic material was discharged under the protection of highly pure nitrogen gas.

Upon determination, it can be found that the resultant composite solid acid catalytic material sample has an HF capacity of 2.58 wt % and an acid density of 1.55×10$^{-3}$ mol $H^+$/g. The properties thereof are listed in Table 2.

Example 2

According to the process in Example 1, phosphotungstic acid was replaced with phosphomolybdic acid to obtain a heteropoly acid-loaded material containing 25% by weight of $H_4SiW_{12}O_{40}$ and 75% by weight of silica gel was obtained and labeled as 25% HSiW/$SiO_2$.

10.0 g of 25% HSiW/$SiO_2$ was loaded into a fixed bed reactor. At normal pressure and at 90° C., nitrogen gas flowed through 25% HSiW/$SiO_2$ bed layer for 22 h. After the treatment, the temperature was increased to 190° C. Under the conditions of a temperature of 190° C., a pressure of 5.5 MPa, and a weight space velocity of 0.5 $h^{-1}$ at which n-butanes flowed through 25% HSiW/$SiO_2$ bed layer, n-butanes containing 450 ppm HF were pumped via a metering pump into the fixed bed reactor for 75 h. Upon purging with highly pure nitrogen gas, the composite solid acid catalytic material was discharged under the protection of highly pure nitrogen gas.

Upon determination, it can be found that the resultant composite solid acid catalytic material sample has an HF capacity of 2.78 wt % and an acid density of 1.74×10$^{-3}$ mol $H^+$/g. The properties thereof are listed in Table 2.

Example 3

According to the process in Example 1, phosphotungstic acid was replaced with phosphomolybdic acid to obtain a heteropoly acid-loaded material containing 25% by weight of $H_3PMo_{12}O_{40}$ and 75% by weight of silica gel was obtained and labeled as 25% HPMo/$SiO_2$.

10.0 g of 25% HPMo/$SiO_2$ was loaded into a fixed bed reactor. At normal pressure and at 120° C., nitrogen gas flowed through 25% HPMo/$SiO_2$ bed layer for 8 h. After the treatment, the temperature was decreased to 75° C. Under the conditions of a temperature of 75° C., a pressure of 3.5 MPa, and a weight space velocity of 7.5 $h^{-1}$ at which propanes flowed through 25% HPW/$SiO_2$ bed layer, propanes containing 650 ppm HF were pumped via a metering pump into the fixed bed reactor for 4 h. Upon purging with highly pure nitrogen gas, the composite solid acid catalytic material was discharged under the protection of highly pure nitrogen gas.

Upon determination, it can be found that the resultant composite solid acid catalytic material sample has an HF capacity of 3.05 wt % and an acid density of 1.94×10$^{-3}$ mol $H^+$/g. The properties and composition thereof are listed in Table 2.

Example 4

According to the process in Example 1, phosphotungstic acid was replaced with phosphomolybdic acid to obtain a heteropoly acid-loaded material containing 25% by weight of $H_4SiMo_{12}O_{40}$ and 75% by weight of silica gel was obtained and labeled as 25% HSiMo/$SiO_2$.

10.0 g of 25% HSiMo/$SiO_2$ was loaded into a fixed bed reactor. At normal pressure and at 130° C., nitrogen gas flowed through 25% HSiMo/SiO bed layer for 6 h. After the treatment, the temperature was decreased to 75° C. Under the conditions of a temperature of 135° C., a pressure of 6.5 MPa, and a weight space velocity of 3.5 $h^{-1}$ at which cyclohexanes flowed through 25% HSiMo/$SiO_2$ bed layer, cyclohexanes containing 252 ppm HCl were pumped via a metering pump into the fixed bed reactor for 20 h. Upon purging with highly pure nitrogen gas, the composite solid acid catalytic material was discharged under the protection of highly pure nitrogen gas.

Upon determination, it can be found that the resultant composite solid acid catalytic material sample has an HCl capacity of 4.68 wt % and an acid density of 1.89×10$^{-3}$ mol $H^+$/g. The properties thereof are listed in Table 2.

Example 5

28.4 g of $H_3PW_{12}O_{40} \cdot 21H_2O$ was weighed and dissolved in 82.0 ml of water to formulate a phosphotungstic acid solution. 25 g of active carbon having a particle size of 20-40 meshes was fed into the suction flask, deaerated for 1.0 h at a vacuity of 0.095 MPa (gauge pressure) and at 85° C., and cooled to room temperature. At normal pressure, the formulated phosphotungstic acid solution was added. After dipping the active carbon support for 3.0 h, then drying in a drying oven for 10 h at 60° C., a heteropoly acid-loaded material containing 50% by weight of $H_3PW_{12}O_{40}$ and 50% by weight of active carbon was obtained and labeled as 50% HPW/C.

10.0 g of 50% HPW/C was loaded into a fixed bed reactor. At normal pressure and at 110° C., nitrogen gas flowed through 50% HPW/C bed layer for 10 h. After the treatment, the temperature was decreased to 75° C. Under the conditions of a temperature of 75° C., a pressure of 2.5 MPa, and a weight space velocity of 4.5 $h^{-1}$ at which benzene flowed through 50% HPW/C bed layer, benzene containing 156 ppm HF were pumped via a metering pump into the fixed bed reactor for 36 h. Upon purging with highly pure nitrogen gas, the composite solid acid catalytic material was discharged under the protection of highly pure nitrogen gas.

Upon determination, it can be found that the resultant composite solid acid catalytic material sample has an HF capacity of 4.05 wt % and an acid density of $2.55 \times 10^{-3}$ mol $H^+/g$. The properties thereof are listed in Table 2.

Example 6

28.4 g of $H_3PW_{12}O_{40} \cdot 21H_2O$ was weighed and dissolved in 82.0 ml of water to formulate a phosphotungstic acid solution. 25 g of γ-alumina having a particle size of 20-40 meshes was fed into the suction flask, deaerated for 1.0 h at a vacuity of 0.095 MPa (gauge pressure) and at 85° C., and cooled to room temperature. At normal pressure, the formulated phosphotungstic acid solution was added. After dipping the γ-alumina support for 2.0 h, then drying in a drying oven for 20 h at 80° C., a heteropoly acid-loaded material containing 50% by weight of $H_3PW_{12}O_{40}$ and 50% by weight of γ-alumina was obtained and labeled as 50% HPW/$Al_2O_3$.

10.0 g of 50% HPW/$Al_2O_3$ was loaded into a fixed bed reactor. At normal pressure and at 110° C., nitrogen gas flowed through 50% HPW/$Al_2O_3$ bed layer for 10 h. After the treatment, the temperature was decreased to 25° C. Under the conditions of a temperature of 25° C., a pressure of 0.5 MPa, and a weight space velocity of 1.5 $h^{-1}$ at which n-butanes flowed through 50% HPW/$Al_2O_3$ bed layer, n-butanes containing 350 ppm HF were pumped via a metering pump into the fixed bed reactor for 110 h. Upon purging with highly pure nitrogen gas, the composite solid acid catalytic material was discharged under the protection of highly pure nitrogen gas.

Upon determination, it can be found that the resultant composite solid acid catalytic material sample has an HF capacity of 3.94 wt % and an acid density of $2.56 \times 10^{-3}$ mol $H^+/g$. The properties thereof are listed in Table 2.

Example 7

22.81 g of $H_3PW_{12}O_{40} \cdot 21H_2O$ was weighed and dissolved in 135.0 ml of ionized water to formulate a phosphotungstic acid solution. 60.3 g of $SiO_2$ having a particle size of 20-40 meshes was fed into the suction flask, treated for 1.0 h at a vacuity of 0.095 MPa and at 75° C., and cooled to room temperature. Under the vacuum condition, the formulated phosphotungstic acid solution was added. After dipping for 1.5 h, then drying in a drying oven for 3 h at 60° C., a heteropoly acid-loaded material containing 25% by weight of $H_3PW_{12}O_{40}$ and 75% by weight of silica gel was obtained and labeled as 25% HPW/$SiO_2$.

2.85 g of $C_{S2}CO_3$ was dissolved in 120.0 ml of ionized water to formulate an aqueous solution of $C_{S2}CO_3$. 25% HPW/$SiO_2$ above was fed into the suction flask, treated for 1.0 h at a vacuity of 0.095 MPa and at 55° C., and cooled to room temperature. Under the vacuum condition, the formulated $C_{S2}CO_3$ solution was added, and the reaction was conducted according to the formula (1) (M herein represents Cs, and x=2.5):

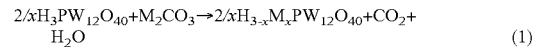

$$2/xH_3PW_{12}O_{40} + M_2CO_3 \rightarrow 2/xH_{3-x}M_xPW_{12}O_{40} + CO_2 + H_2O \qquad (1)$$

After dipping for 3.0 h, then drying in a drying oven for 8 h at 50° C., a $Cs_{2.5}H_{0.5}PW_{12}O_{40}$/$SiO_2$ heteropoly acid salt-loaded material was obtained and labeled as $Cs_{2.5}H_{0.5}PW$/$SiO_2$.

10.0 g of $Cs_{2.5}H_{0.5}PW$/$SiO_2$ was loaded into a fixed bed reactor. At normal pressure and at 110° C., nitrogen gas flowed through $Cs_{2.5}H_{0.5}PW$/$SiO_2$ bed layer for 6 h. After the treatment, the temperature was increased to 136° C. Under the conditions of a temperature of 136° C., a pressure of 4.5 MPa, and a weight space velocity of 2.5 $h^{-1}$ at which isobutanes flowed through $Cs_{2.5}H_{0.5}PW$/$SiO_2$ bed layer, isobutanes containing 350 ppm HF were pumped via a metering pump into the fixed bed reactor for 16 h. Upon purging with highly pure nitrogen gas, the solid acid material was discharged under the protection of highly pure nitrogen gas.

Upon determination, it can be found that the resultant solid acid sample has an HF capacity of 2.89 wt % and an acid density (mol $H^+/g$) of $1.49 \times 10^{-3}$ mol/g, which is higher than the USY molecular sieve catalyst ($0.4 \times 10^{-3}$) by an order of magnitude. The properties of the composite solid acid are listed in Table 2.

Example 8

25.4 g of $H_3PW_{12}O_{40} \cdot 21H_2O$ was weighed and dissolved in 150.0 ml of deionized water to formulate an aqueous solution of $H_3PWO_{40}$. 67.1 g of $SiO_2$ having a particle size of 20-40 meshes was fed into the suction flask, treated for 1.0 h at a vacuity of 0.095 MPa and at 75° C., and cooled to room temperature. Under the vacuum condition, the formulated $H_3PW_{12}O_{40}$ solution was added. After dipping for 1.5 h, then drying in a drying oven for 3 h at 60° C., a heteropoly acid-loaded material containing 25% by weight of $H_3PW_{12}O_{40}$ and 75% by weight of silica gel was obtained and labeled as 25% HPW/$SiO_2$.

1.61 g of $K_2CO_3$ was dissolved in 145.0 ml of ionized water to formulate an aqueous solution of $K_2CO_3$. 25% HPW/$SiO_2$ above was fed into the suction flask, treated for 1.0 h at a vacuity of 0.095 MPa and at 55° C., and cooled to room temperature. Under the vacuum condition, the formulated $K_2CO_3$ solution was added, and the reaction was conducted according to the formula (1) (M herein represents K, and x=3.0). After dipping for 3.0 h, then drying in a drying oven for 8 h at 50° C., a $K_3PW_{12}O_{40}$/$SiO_2$ heteropoly acid salt-loaded material was obtained and labeled as $K_3PW$/$SiO_2$.

10.0 g of $K_3PW$/$SiO_2$ was loaded into a fixed bed reactor. At normal pressure and at 90° C., nitrogen gas flowed through the $K_3PW$/$SiO_2$ bed layer for 6 h. After the treatment, the temperature was increased to 95° C. Under the conditions of a temperature of 135° C., a pressure of 6.5 MPa, and a weight space velocity of 7.5 $h^{-1}$ at which isobutanes flowed through $K_3PW$/$SiO_2$ bed layer, isobutanes containing 1450 ppm HF were pumped via a metering pump into the fixed bed reactor for 5 h. Upon purging with highly pure nitrogen gas, the solid acid material was discharged under the protection of highly pure nitrogen gas.

Upon determination, it can be found that the resultant solid acid sample has an HF capacity of 2.95 wt % and an acid density (mol $H^+$/g) of $1.56 \times 10^{-3}$ mol/g. The properties of the composite solid acid are listed in Table 2.

Example 9

17.1 g of $H_3PMo_{12}O_{40} \cdot 17H_2O$ was weighed and dissolved in 100.0 ml of deionized water to formulate an aqueous solution of $H_3PWO_{40}$. 44.0 g of $Al_2O_3$ having a particle size of 20-40 meshes was fed into the suction flask, treated for 1.0 h at a vacuity of 0.095 MPa and at 75° C., and cooled to room temperature. Under the vacuum condition, the formulated $H_3PW_{12}O_{40}$ solution was added. After dipping for 1.5 h, then drying in a drying oven for 2 h at 60° C., a supported-type heteropoly acid containing 25% by weight of $H_3PMo_{12}O_{40}$ and 75% by weight of alumina was obtained and labeled as 25% HPMo/$Al_2O_3$.

3.26 g of $C_{S2}CO_3$ was dissolved in 97.0 ml of ionized water to formulate an aqueous solution of $C_{S2}CO_3$. 25% HPMo/$SiO_2$ above was fed into the suction flask, treated for 1.0 h at a vacuity of 0.095 MPa and at 55° C., and cooled to room temperature. Under the vacuum condition, the formulated $C_{S2}CO_3$ solution was added, and the reaction was conducted according to the formula (2) (M herein represents Cs, and x=2.5):

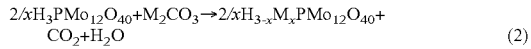

(2)

After dipping for 3.5 h, then drying in a drying oven for 9 h at 50° C., a $C_{S2.5}H_{0.5}PMo_{12}O_{40}/Al_2O_3$ heteropoly acid salt-loaded material was obtained and labeled as $Cs_{2.5}H_{0.5}PMo/Al_2O_3$.

10.0 g of $Cs_{2.5}H_{0.5}PW/Al_2O_3$ was loaded into a fixed bed reactor. At normal pressure and at 120° C., nitrogen gas flowed through $Cs_{2.5}H_{0.5}PW/Al_2O_3$ bed layer for 8 h. After the treatment, the temperature was decreased to 75° C. Under the conditions of a temperature of 75° C., a pressure of 3.5 MPa, and a weight space velocity of 1.0 $h^{-1}$ at which propanes flowed through $Cs_{2.5}H_{0.5}PW/Al_2O_3$ bed layer, propanes containing 850 ppm HF were pumped via a metering pump into the fixed bed reactor for 6 h. Upon purging with highly pure nitrogen gas, the solid acid material was discharged under the protection of highly pure nitrogen gas.

Upon determination, it can be found that the resultant solid acid sample has an HF capacity of 2.74 wt % and an acid density (mol $H^+$/g) of $1.43 \times 10^{-3}$ mol/g. The properties of the composite solid acid are listed in Table 2.

Example 10

17.23 g of $H_4SiW_{12}O_{40} \cdot 15H_2O$ was weighed and dissolved in 97.0 ml of deionized water to formulate an aqueous solution of $H_3SiWO_{40}$. 47.3 g of active carbon having a particle size of 20-40 meshes was fed into the suction flask, treated for 1.0 h at a vacuity of 0.095 MPa and at 95° C., and cooled to room temperature. Under the vacuum condition, the formulated $H_3PW_{12}O_{40}$ solution was added. After dipping for 2.0 h, then drying in a drying oven for 4 h at 60° C., a heteropoly acid-loaded material containing 50% by weight of $H_3SiW_{12}O_{40}$ and 50% by weight of active carbon was obtained and labeled as 25% HSiW/C.

2.24 g of $C_{S2}CO_3$ was dissolved in 95.0 ml of ionized water to formulate an aqueous solution of $C_{S2}CO_3$. 25% HSiW/C above was fed into the suction flask, treated for 1.0 h at a vacuity of 0.095 MPa and at 95° C., and cooled to room temperature. Under the vacuum condition, the formulated $C_{S2}CO_3$ solution was added, and the reaction was conducted according to the formula (3) (M herein represents Cs, and x=2.5):

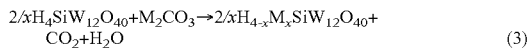

(3)

After dipping for 3.0 h, then drying in a drying oven for 10 h at 60° C., a $C_{S2.5}H_{1.5}PW_{12}O_{40}$/C heteropoly acid salt-loaded material was obtained and labeled as $Cs_{2.5}H_{1.5}PW$/C.

10.0 g of $Cs_{2.5}H_{0.5}PW$/C was loaded into a fixed bed reactor. At normal pressure and at 120° C., nitrogen gas flowed through $Cs_{2.5}H_{1.5}PW$/C bed layer for 8 h. After the treatment, the temperature was increased to 195° C. Under the conditions of a temperature of 195° C., a pressure of 5.5 MPa, and a weight space velocity of 1.5 $h^{-1}$ at which cyclohexanes flowed through $Cs_{2.5}H_{1.5}PW$/C bed layer, cyclohexanes containing 252 ppm HCl were pumped via a metering pump into the fixed bed reactor for 115 h. Upon purging with highly pure nitrogen gas, the solid acid material was discharged under the protection of highly pure nitrogen gas.

Upon determination, it can be found that the resultant solid acid sample has an HCl capacity of 4.73 wt % and an acid density (mol $H^+$/g) of $1.44 \times 10^{-3}$ mol/g. The properties of the composite solid acid are listed in Table 2.

Example 11

16.7 g of $H_4SiMo_{12}O_{40} \cdot 14H_2O$ was weighed and dissolved in 39.0 ml of deionized water to formulate an aqueous solution of $H_3SiMoO_{40}$. 14.7 g of silicon oxide having a particle size of 20-40 meshes was fed into the suction flask, treated for 1.0 h at a vacuity of 0.095 MPa and at 95° C., and cooled to room temperature. Under the vacuum condition, the formulated $H_4SiMo_{12}O_{40}$ solution was added. After dipping for 2.0 h, then drying in a drying oven for 5 h at 55° C., a heteropoly acid-loaded material containing 50% by weight of $H_4SiMo_{12}O_{40}$ and 50% by weight of silicon oxide was obtained and labeled as 50% HSiMo/$SiO_2$.

1.38 g of $K_2CO_3$ was dissolved in 38.0 ml of ionized water to formulate an aqueous solution of $K_2CO_3$. 50% HSiMo/$SiO_2$ above was fed into the suction flask, treated for 1.0 h at a vacuity of 0.095 MPa and at 65° C., and cooled to room temperature. Under the vacuum condition, the formulated $K_2CO_3$ solution was added, and the reaction was conducted according to the formula (4) (M herein represents K, and x=2.5):

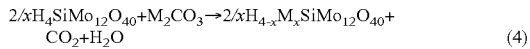

(4)

After dipping for 3.0 h, then drying in a drying oven for 10 h at 60° C., a $K_{2.5}H_{1.5}SiMo_{12}O_{40}/SiO_2$ heteropoly acid salt-loaded material was obtained and labeled as $K_{2.5}H_{1.5}PMo/SiO_2$.

10.0 g of $K_{2.5}H_{1.5}SiMo/SiO_2$ were loaded into a fixed bed reactor. At normal pressure and at 110° C., nitrogen gas flowed through $K_{2.5}H_{1.5}SiMo/SiO_2$ bed layer for 12 h. After the treatment, the temperature was decreased to 45° C. Under the conditions of a temperature of 45° C., a pressure of 1.5 MPa, and a weight space velocity of 1.5 $h^{-1}$ at which isobutanes flowed through $K_{2.5}H_{1.5}SiMo/SiO_2$ bed layer, isobutanes containing 350 ppm HF were pumped via a metering pump into the fixed bed reactor for 28 h. Upon purging with highly pure nitrogen gas, the solid acid material was discharged under the protection of highly pure nitrogen gas.

Upon determination, it can be found that the resultant solid acid sample has an HF capacity of 4.38 wt % and an acid density (mol H$^+$/g) of 2.6×10$^{-3}$ mol/g. The properties of the composite solid acid are listed in Table 2.

Comparative Example 1

The USY molecular sieve catalyst prepared according to the prior art has an acid sites density of 0.4×10$^{-3}$ mol, and the properties thereof are listed in Table 2.

Comparative Example 2

The heteropoly acid-loaded material 25% HPW/SiO$_2$ prepared according to the process in Example 1 and containing 25% by weight of H$_3$PW$_{12}$O$_{40}$ and 75% by weight of silica gel has an acid sites density of 0.26×10$^{-3}$ mol, and the properties thereof are listed in Table 2.

Comparative Example 3

The Cs$_{2.5}$H$_{0.5}$PW/SiO$_2$ heteropoly acid salt-loaded material prepared according to the process in Example 7 has an acid sites density of 0.04×10$^{-3}$ mol, and the properties thereof are listed in Table 2.

TABLE 2

Acidity properties of the composite solid acid material and the amount of the loaded inorganic acid

| | Porous inorganic support, wt % | Heteropoly acid, wt. % | Inorganic acid, wt. % | Acid sites density (molH$^+$/g) | Acid strength (−H$_o$) | Acid sites type | Specific surface area (m$^2$/g) |
|---|---|---|---|---|---|---|---|
| Example 1 | 73.12 | 24.30 | 2.58 | 1.55 × 10$^{-3}$ | 13.16 | B | 352 |
| Example 2 | 72.92 | 24.28 | 2.78 | 1.74 × 10$^{-3}$ | 13.16 | B | 347 |
| Example 3 | 72.73 | 24.22 | 3.05 | 1.94 × 10$^{-3}$ | — | B | 349 |
| Example 4 | 71.67 | 23.65 | 4.68 | 1.89 × 10$^{-3}$ | 13.16 | B | 355 |
| Example 5 | 47.97 | 47.97 | 4.05 | 2.55 × 10$^{-3}$ | — | B | 455 |
| Example 6 | 48.06 | 48.00 | 3.94 | 2.56 × 10$^{-3}$ | 13.16 | B | 312 |
| Example 7 | 74.82 | 22.29 | 2.89 | 1.49 × 10$^{-3}$ | 14.52 | B | 378 |
| Example 8 | 78.77 | 18.28 | 2.95 | 1.56 × 10$^{-3}$ | 13.75 | B | 369 |
| Example 9 | 73.96 | 23.29 | 2.74 | 1.43 × 10$^{-3}$ | — | B | 337 |
| Example 10 | 73.45 | 21.82 | 4.73 | 1.44 × 10$^{-3}$ | 14.52 | B | 461 |
| Example 11 | 51.97 | 43.65 | 4.38 | 2.60 × 10$^{-3}$ | — | B | 355 |
| Com. Exp. 1 | — | — | — | 0.4 × 10$^{-3}$ | — | B & L | 625 |
| Com. Exp. 2 | 75.0 | 25.0 | 0 | 0.26 × 10$^{-3}$ | — | B | 358 |
| Com. Exp. 3 | 77.02 | 22.98 | 0.00 | 0.04 × 10$^{-3}$ | 14.52 | B | 358 |

B: Brönsted acid,
L is Lewis acid

Examples 12 and 13 state the performances of the composite solid acid catalyst prepared according to the present invention.

Example 12

The preparation conditions in Example 1 were repeated to obtain a composite solid acid catalyst, but the catalyst was not discharged from the reactor. At the same temperature and pressure as required for the alkylation reaction of isobutane and butylene (see Table 3), isobutane and butylene were fed via a metering pump into the same reactor for the alkylation reaction. After 72 and 300 h, a gas chromatograph was used to analyze the liquid product and the composition of the reaction tail gas. The reaction results are listed in Table 3.

Example 13

The preparation conditions in Example 7 were repeated to obtain a composite solid acid catalyst, but the catalyst was not discharged from the reactor. At the same temperature and pressure as required for the alkylation reaction of isobutane and butylene (see Table 3), isobutane and butylene were fed via a metering pump into the same reactor for the alkylation reaction. After 100 h, a gas chromatograph was used to analyze the liquid product and the composition of the reaction tail gas. The reaction results are listed in Table 3.

Comparative Example 4

According to the preparation conditions in Example 1, 25% HPW/SiO$_2$ was firstly obtained. Then 10.0 g of said solid acid catalyst was loaded into the fixed-bed reactor, and nitrogen gas was fed therein. At the same temperature and pressure as required for the alkylation reaction of isobutane and butylene and as those in Example 12 (see Table 3), isobutane and butylene were fed via a metering pump into the reactor for the alkylation reaction. Meanwhile, the feeding of nitrogen gas stopped. After 20 h, a gas chromatograph was used to analyze the liquid product and the composition of the reaction tail gas. The reaction results are listed in Table 3.

Comparative Example 5

According to the preparation conditions in Example 7, Cs$_{2.5}$H$_{0.5}$PW/SiO$_2$ was firstly obtained. Then 10.0 g of said solid acid catalyst was loaded into the fixed-bed reactor, and nitrogen gas was fed therein. At the same temperature and pressure as required for the alkylation reaction of isobutane and butylene and as those in Example 6 (see Table 3), isobutane and butylene were fed via a metering pump into the reactor for the alkylation reaction. Meanwhile, the feeding of nitrogen gas stopped. After 20 h, a gas chromatograph was used to analyze the liquid product and the composition of the reaction tail gas. The reaction results are listed in Table 3.

TABLE 3

Alkylation reaction results

|  |  | Example 12 | Example 13 | Com.Exp.4 | Com.Exp.5 |
|---|---|---|---|---|---|
| Reaction conditions | Acid sites density of the catalyst (mol $H^+$/g) | $1.55 \times 10^{-3}$ | $1.55 \times 10^{-3}$ | $1.49 \times 10^{-3}$ | $0.26 \times 10^{-3}$ | $0.04 \times 10^{-3}$ |
|  | Temperature, °C. | 136 | 140 | 136 | 136 | 136 |
|  | Pressure, MPa | 4.5 | 6.5 | 4.5 | 4.5 | 4.5 |
|  | Weight space velocity, $h^{-1}$ | 4.0 | 10.0 | 4.0 | 4.0 | 4.0 |
|  | Alkane/alkene, molar ratio | 25.0 | 125.0 | 25.0 | 25.0 | 25.0 |
|  | Reaction time, h | 72 | 300 | 100 | 20 | 20 |
| $C^=$ alkene conversion rate, wt % |  | 100.0 | 100.0 | 100.0 | 100.0 | 100.0 |
| Alkylate yield, g/g |  | 2.01 | 2.00 | 2.01 | 1.99 | 1.98 |
| Reaction product distribution, wt % |  |  |  |  |  |  |
|  | $C_5$ | 2.15 | 1.42 | 2.75 | 3.43 | 3.61 |
|  | $C_6$ | 3.21 | 3.35 | 3.56 | 4.65 | 4.77 |
|  | $C_7$ | 4.66 | 4.75 | 4.89 | 5.68 | 5.75 |
|  | $C_8$ | 85.66 | 85.94 | 83.66 | 77.77 | 74.77 |
|  | $C_9^+$ | 4.32 | 4.54 | 5.14 | 8.47 | 11.10 |
|  | $C_8^=$ | 0.00 | 0.00 | 0.00 | 0.00 | 0.00 |
|  | TMP/DMH | 7.12 | 7.19 | 6.85 | 5.09 | 4.89 |
| Octane number of alkylate |  |  |  |  |  |  |
|  | RON | 95.6 | 95.8 | 95.1 | 94.1 | 92.3 |
|  | MON | 93.4 | 93.6 | 93.0 | 92.0 | 90.1 |

TMP: trimethylpentane,
DMH: dimethylhexane,
RON: research octane number,
MON: motor octane number According to the reaction results in Table 3, it can be seen that, as compared with the conventional supported-type heteropoly acid catalyst, the composite solid acid catalyst prepared according to the present invention shows a higher TMP/DMH ratio and a higher octane number in the alkylation reaction, which shows that the composite solid acid catalyst with the high acid sites density has a better catalytic activity and selectivity in the alkylation.

The acidity of the reaction product has detected during the alkylation all along, and the reaction product shows neutrality all the while, which means no acid loss from the composite solid acid catalyst. After 300 h, the conversion of the alkylation which remains stable also show that the Brönsted acid supported on the composite solid acid catalyst is stable.

The invention claimed is:

1. A composite solid acid catalyst consisting of from 50% to 80% by weight of a porous inorganic support, from 15% to 48% by weight of a heteropoly compound loaded thereon, and from 2% to 6% by weight of an inorganic acid, said heteropoly compound having a general formula of $M_xH_{8-n-x}[AB_{12}O_{40}]$, wherein A is a heteroatom P or Si, B is polyatom W or Mo, M is selected from the group consisting of alkali metals of Li, Na, K, Rb and Cs, alkali earth metals of Be, Mg, Ca, Sr and Ba, and $NH_4$, n is the valence state of A, which is 4 or 5, x is any number from 0 to 4, and said inorganic acid is selected from HF or HCl, and said porous inorganic support is one or more selected from silicon oxide, alumina, active carbon, magnesium oxide, titanium oxide, natural or artificially synthetic aluminosilicate zeolite, molecular sieve, carbon fiber and natural clay, or mixtures thereof;

wherein the composite solid acid catalyst has the acid sites type of Brönsted acid and has an acid sites density of not less than $1.4 \times 10^{-3}$ mol $H^+$/g.

2. The composite solid acid catalyst according to claim 1, wherein said inorganic acid is in an amount of from 2% to 5% by weight.

3. The composite solid acid catalyst according to claim 1, wherein the porous inorganic support is one or more selected from the group consisting of active carbon, silicon oxide, alumina and zeolite.

4. The composite solid acid catalyst according to claim 1, characterized in that the heteropoly compound is a heteropoly acid.

5. The composite solid acid catalyst according to claim 4, wherein the heteropoly acid is phosphotungstic acid.

6. The composite solid acid catalyst according to claim 1, wherein the heteropoly compound is a heteropoly acid salt, wherein M in the general formula is selected from the group consisting of K, Cs and $NH_4$; and x is a number from 2 to 4.

7. The composite solid acid catalyst according to claim 1, wherein the heteropoly compound is a heteropoly acid salt, wherein A in the general formula is P; B is W; and M is selected from the group consisting of alkali metals of Li, Na, K, Rb and Cs, alkali earth metals of Be, Mg, Ca, Sr and Ba, and $NH_4$.

8. The composite solid acid catalyst according to claim 6 or 7, wherein A in the general formula is P; B is W; and M is selected from the group consisting of K, Cs and $NH_4$.

9. A process for preparing a composite solid acid catalyst, comprising the steps of
(1) loading a heteropoly compound onto a porous inorganic support to obtain a heteropoly compound-loaded material, wherein said heteropoly compound having a general formula of $M_xH_{8-n-x}[AB_{12}O_{40}]$, in which
A is a heteroatom P or Si,
B is polyatom W or Mo,
M is selected from the group consisting of alkali metals of Li, Na, K, Rb and Cs, alkali earth metals of Be, Mg, Ca, Sr and Ba, and $NH_4$,
n is the valence state of A, which is 4 or 5,
x is any number from 0 to 4, and
said porous inorganic support is one or more selected from silicon oxide, alumina, active carbon, magnesium oxide, titanium oxide, natural or artificially synthetic aluminosilicate zeolite, molecular sieve, carbon fiber and natural clay, or mixtures thereof; and said porous inorganic support is in an amount of from 50% to 80% by weight, and the amount of the loaded heteropoly compound ranges from 15% to 48% by weight, relative to the weight of the composite solid acid catalyst;
(2) dissolving an inorganic acid selected from HF or HCl in hydrocarbons including saturated alkanes, cycloalkanes, aromatic hydrocarbons or petroleum ethers; and
(3) contacting said hydrocarbons comprising the inorganic acid with the heteropoly compound-loaded material to obtain a composite solid acid catalyst simultaneously comprising the inorganic acid and the heteropoly compound, wherein the amount of the loaded inorganic acid ranges from 2% to 6% by weight relative to the weight of the composite solid acid catalyst; wherein the composite solid acid catalyst has the acid sites type of Brönsted acid and has an acid sites density of not less than $1.4 \times 10^{-3}$ mol $H^+$/g.

10. The process according to claim 9, wherein the amount of the loaded inorganic acid ranges from 2% to 5% by weight relative to the weight of the composite solid acid catalyst.

11. The process according to claim 9, wherein said porous inorganic support is one or more selected from the group consisting of active carbon, silicon oxide, alumina and zeolite.

12. The process according to claim 1 or 9, wherein said hydrocarbons are selected from the group consisting of propane, n-butane, isobutane, pentane, hexane, cyclopentanes, cyclohexane, benzene, toluene and xylene.

13. The process according to claim 9, wherein the inorganic acid in the hydrocarbons in step (3) is in an amount of from 20 to 2,000 ppm calculated by $H^+$.

14. The process according to claim 13, wherein the inorganic acid in the hydrocarbons in step (3) is in an amount of from 100 to 1,500 ppm calculated by $H^+$.

15. The process according to claim 9, wherein said contacting is conducted in a fixed-bed reactor, a moving bed, a fluidized-bed or a triphase slurry bed reactor.

16. The process according to claim 15, wherein said contacting is conducted in a fixed-bed reactor.

17. The process according to claim 9, wherein said contacting is conducted under the conditions of a temperature ranging from 20 to 250° C., a pressure ranging from 0.05 to 7.0 MPa, a weight space velocity of hydrocarbons containing the inorganic acid ranging from 0.1 to 10 $h^{-1}$, and contacting time ranging from 1 to 120 h.

18. The process according to claim 9, wherein said contacting is conducted under the conditions of a temperature ranging from 30 to 200° C., a pressure ranging from 0.1 to 6.0 MPa, a weight space velocity of hydrocarbons containing the inorganic acid ranging from 1.0 to 8.01 $h^{-1}$, and contacting time ranging from 4 to 80 h.

19. The process according to claim 9, wherein said step (1) is conducted as follows:
i) homogeneously loading a heteropoly acid selected from the group consisting of phosphotungstic acid, phosphomolybdic acid, silicotungstic acid and silicomolybdic acid onto a porous inorganic support by a conventional immersion method to obtain a heteropoly compound-loaded material, wherein the amount of the loaded heteropoly acid ranges from 15% to 48% by weight relative to the weight of the composite solid acid catalyst; and
ii) optionally, contacting said heteropoly compound-loaded material with the solution of alkali metal salts, alkali earth metal salts or ammonium salts by a conventional immersion method so as to convert at least a part of the loaded heteropoly acid into a heteropoly acid salt.

20. The process according to claim 19, wherein the heteropoly acid is phosphotungstic acid; and said alkali metal salts, alkali earth metal salts or ammonium salts are carbonates of K, Cs or $NH_4$.

* * * * *